| United States Patent [19] | [11] Patent Number: 4,898,802 |
| Hsieh et al. | [45] Date of Patent: Feb. 6, 1990 |

[54] TONER COMPOSITIONS WITH ORGANO BORON NEGATIVE CHARGE ENHANCING ADDITIVES

[75] Inventors: Bing R. Hsieh, Webster; Robert J. Gruber; John L. Haack, both of Pittsford, all of N.Y.

[73] Assignee: Xerox Corporation, Stamford, Conn.

[21] Appl. No.: 354,181

[22] Filed: May 22, 1989

[51] Int. Cl.$^4$ .............................................. G03G 9/08
[52] U.S. Cl. ................................... 430/110; 430/115; 430/903
[58] Field of Search ...................... 430/110, 903, 115

[56] References Cited

U.S. PATENT DOCUMENTS

| | | | |
|---|---|---|---|
| 4,206,064 | 6/1980 | Kiuchi et al. | 430/106 |
| 4,411,974 | 10/1983 | Lu et al. | 430/106 |
| 4,525,446 | 6/1985 | Uytterhoeven et al. | 430/117 |
| 4,737,432 | 4/1988 | Tanaka et al. | 430/110 |
| 4,767,688 | 8/1988 | Hashimoto et al. | 430/110 |
| 4,845,003 | 7/1989 | Kiriu et al. | 430/110 |

*Primary Examiner*—J. David Welsh
*Attorney, Agent, or Firm*—E. O. Palazzo

[57] ABSTRACT

A negatively charged toner composition comprised of resin particles, pigment particles, and as a charge enhancing additive certain salts of 5,5'-spirobi(5H-dibenzoborole).

26 Claims, No Drawings

TONER COMPOSITIONS WITH ORGANO BORON NEGATIVE CHARGE ENHANCING ADDITIVES

BACKGROUND OF THE INVENTION

The invention is generally directed to toner compositions, and more specifically, the present invention is directed to developer and toner compositions containing therein charge enhancing additives, which impart, or assist in imparting a negative charge to the toner resin particles. In one embodiment, there are provided in accordance with the present invention toner compositions comprised of resin particles, pigment particles, and the salts of certain spiro-borate compounds as negative charge enhancing additives. The aforementioned toner compositions usually contain pigment particles comprised of, for example, carbon black, magnetites, cyan, magenta, yellow, blue, green, red, or brown components and mixtures thereof, thereby providing for the development of black or colored images. The borate salts of the present invention possess a number of advantages including, for example, they are colorless, unlike some dye-based compounds which are of various deep colors. In addition, the borate salts of the present invention are readily solubilized in common organic solvents and are compatible with various toner resins enabling the simple economical processing thereof. Also, the toner compositions of the present invention possess excellent admix characteristics, and maintain their negative triboelectric charges for an extended number of imaging cycles exceeding, for example, 50,000. The toner and developer compositions of the present invention can be selected for electrophotographic, especially xerographic, imaging and printing processes.

Developer compositions with charge enhancing additives, which impart a positive charge to the toner resin, are well known. Thus, for example, there is described in U.S. Pat. No. 3,893,935 the use of quaternary ammonium salts as charge control agents for electrostatic toner compositions. There is also described in U.S. Pat. No. k 2,986,521 reversal developer compositions comprised of toner resin particles coated with finely divided colloidal silica. According to the disclosure of this patent, the development of electrostatic latent images on negatively charged surfaces is accomplished by applying a developer composition having a positively charged triboelectric relationship with respect to the colloidal silica.

Also, there are disclosed in U.S. Pat. No. 4,338,390, the disclosure of which is totally incorporated herein by reference, developer compositions containing as charge enhancing additives organic sulfate and sulfonates, which additives can impart a positive charge to the toner composition. Further, there are disclosed in U.S. Pat. No. 4,298,672 positively charged toner compositions with resin particles and pigment particles, and as charge enhancing additives ·alkyl pyridinium compounds. Additionally, other documents disclosing positively charged toner compositions with charge control additives include U.S. Pat. Nos. 3,944,493; 4,007,293; 4,079,014 and 4,394,430.

Moreover, toner compositions with negative charge enhancing additives are known, reference for example U.S. Pat. Nos. 4,411,974 and 4,206,064, the disclosures of which are totally incorporated herein by reference. The '974 patent discloses negatively charged toner compositions comprised of resin particles, pigment particles, and as a charge enhancing additive ortho-halo phenyl carboxylic acids. Similarly, there is disclosed in the '064 patent toner compositions with chromium, cobalt, and nickel complexes of salicylic acid as negative charge enhancing additives.

There is illustrated in U.S. Pat. No. 4,404,271, the disclosure of which is totally incorporated herein by reference, a complex system for developing electrostatic images with a toner which contains a metal complex represented by the formula in column 2, for example, and wherein ME can be chromium, cobalt or iron. Additionally, other patents disclosing various metal containing azo dyestuff structures wherein the metal is chromium or cobalt include Nos. 2,891,939; 2,871,233; 2,891,938; 2,933,489; 4,053,462 and 4,314,937. Also, in U.S. Pat. No. 4,433,040, the disclosure of which is totally incorporated herein by reference, there are illustrated toner compositions with chromium and cobalt complexes of azo dyes as negative charge enhancing additives.

Other prior art includes Japanese Publication No. 54-145542 which illustrates a negatively chargeable toner consisting of a resin, a colorant, and the charge control agent pyridoxine aliphatic acid ester; East German Patent Publication 218697 relating to liquid developers with charge control additives with structural units of formulas (I), (II) and (III), and which contains olefinically polymerizable bonds; U.S. Pat. Nos. 3,850,642 relating to multilayer sensitive elements wit ionizable salts, acids, esters, and surfactants as charge control agents; 2,970,802 illustrating a composition for the control of hypercholestermia, which composition consists of a nontoxic gelatin containing aluminum nicotinate; and 3,072,659 which discloses a method of preparing aluminum salts of nicotinic acid.

As a result of a patentability search, there were located U.S. Pat. Nos. 4,525,446 relating to a liquid developer with an onium salt polymer and an anion, and more specifically, wherein iodide anions of a quaternized polymer are replaced with tetraphenyl boride anions, see column 7 for example; 4,737,432 directed to a toner with certain borates, such as diorganotin borate; and 4,767,688 relating to a developer with charge-exchange control agents comprising a borate containing an organic anion, including tetraphenylboron anion with sodium or potassium as its corresponding cationic component.

Furthermore, there are disclosed in U.S. Pat. No. 4,623,606, toner compositions with negative charge enhancing additives, the disclosure of which is totally incorporated herein by reference, containing therein as negative charge enhancing additives iron complexes, including the iron complex of azo dyes prepared from coupling diazzotized substituted amino phenols with substituted naphthols.

Although many charge enhancing additives are known, there continues to be a need for new additives, especially those that impart negative charges to toner resin particles. Additionally, there is a need for negative charge enhancing additives which are useful for incorporation into black, or colored toner compositions. Moreover, there is a need for toners containing charge enhancing additives with very light colors thereby avoiding or minimizing impairment of the color of the toner particles. There is also a need for toner compositions with negative charge enhancing additives that possess acceptable triboelectric charging characteristics, and suitable admixing properties. Moreover, there continues to be a need for humidity insensitive negative charged toner and developer compositions. Further, there is a need for charge enhancing additives which can be easily and permanently dispersed into toner resin particles. There also is a need for negatively charged black, and colored toner compositions that are useful for incorporation into various imaging processes, inclusive of color xerography, as illustrated in U.S. Pat. No. 4,078,929, the disclosure of which is totally incorporated herein by reference; laser printers; and additionally, the toner compositions of the present invention are useful in imaging apparatuses having incorporated therein layered photoresponsive imaging members, such as the members illustrated in U.S. Pat. No. 4,265,990, the disclosure of which is totally incorporated herein by reference. Furthermore, there is a need for negatively charged toner compositions with desirable and rapid toner admix charging characteristics.

SUMMARY OF THE INVENTION

It is an object of the present invention to provide toner and developer compositions with negative charge enhancing additives.

In another object of the present invention there are provided negatively charged toner compositions useful for the development of electrostatic latent images including color images.

In yet another object of the present invention there are provided negatively charged toner compositions containing as charge enhancing additives the salts of spirobi(5H-dibenzoborole) anion and the derivatives thereof, which additives are believed to be nontoxic.

Also, in another object of the present invention there are provided developer compositions with negatively charged toner particles, carrier particles, and as charge enhancing additives the salts of spirobi(5H-dibenzoborole) and the derivatives thereof.

In yet a further object of the present invention there are provided humidity insensitive negatively charged toner compositions with desirable admix properties, equal to or less than 2 minutes for example, and acceptable triboelectric charging characteristics.

Additionally, in a further object of the present invention there are provided negatively charged magnetic toner compositions, and negatively charged colore toner compositions conftaining therein the salts of spirobi(5H-dibenzoborole) and similar additives.

Furthermore, in yet another object of the present invention there are provided toner compositions with negative charge enhancing additives, which compositions are useful in a variety of electrostatic imaging and printing processes, including color xerography.

These and other objects of the present invention are accomplished by providing toner compositions comprised of resin particles, pigment particles, and as charge enhancing additives the salts of 5,5'-spirobi(5H-dibenzoborole), including bis(2,2'-biphenylylene)borate or bis(2,2'-biphenylene)borate and the derivatives thereof. Examples of the aforementioned salts include those of the following formulas

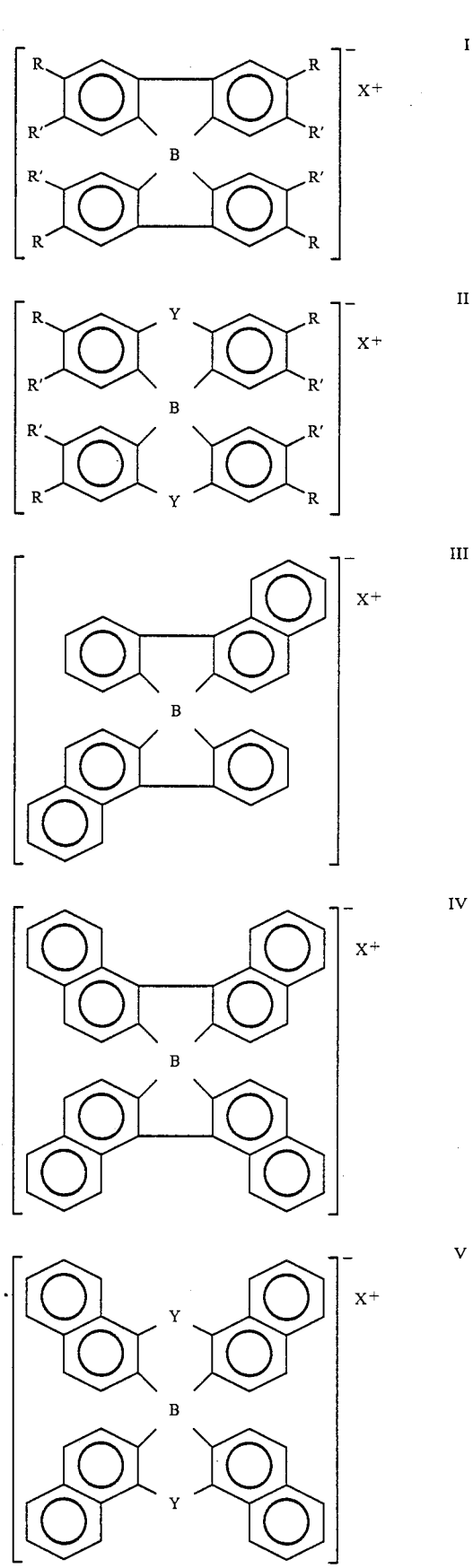

where R and R' are independently selected from the group consisting of hydrogen, an aliphatic hydrocarbon, particularly an alkyl or alkoxy substituent of from 1 to about 25 carbon atoms including, for example, methyl, ethyl, $CH_3(CH_2)_n$, wherein n is a number of from 2 to about 25, as well as the isomers thereof, methoxy, ethoxy, propoxy, and the like, and a halide such as fluoride; Y is alkylene, such as methylene and hetroatoms such as oxygen, sulfur, alkylated nitrogen, and the like; X is a cation including, for example, alkali metals, such as lithium, sodium, potassium, and cesium; ammonium, and $NR_4$ wherein R is alkyl.

Three preparation schemes can be selected for obtaining the o,o'-di-bromobiphenyls, which are interneduates for formulating the charge enhancing additives illustrated herein. As illustrated in Scheme I, bromination of properly substituted biphenyls, such as 3,3'-dimethoxybiphenyl or 4,4'-di-t-butylbiphenyl with two equivalents of bromine in acetic acid at room temperature provides 3,3'-dimethoxy-6,6'-dibromo-biphenyl or 4,4'-di-t-butyl-6,6'-dibromo-biphenyl, respectively

SCHEME I

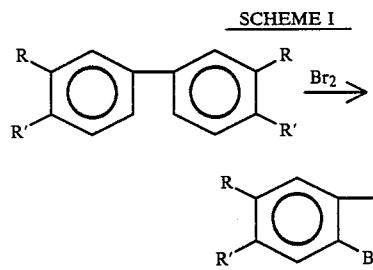

(1) R = $OCH_3$, R' = H
(2) R = H, R' = t-Butyl

Alternatively, derivatives of o,o'-di-bromobiphenyls can be obtained from commercially available o,o'-dihydroxybiphenyls by, for example, heating a mixture of dibromo-triphenylphosphorane (two equivalents) and one equivalent of 2,2'-dihydroxy-biphenyl or 2,2'-dihydroxy-1,1'-binaphthyl at 300° C. to provide the corresponding o,o'-dibromo compound in accordance with reaction Scheme II that follows. Thirdly, derivatives of o,o'-di-bromobiphenyls can be obtained by the self-coupling reaction of 1,2-dibromobenzenes, for example, the coupling reaction of 1,2-dibromobenzene in the presence of n-butyllithium to yield 2,2'-dibromobiphenyl.

SCHEME II

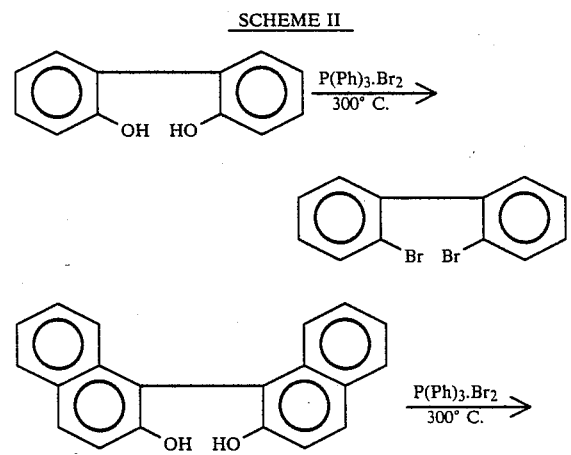

-continued
SCHEME II

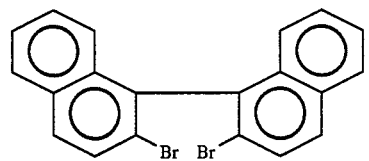

SCHEME III

The metal-halogen exchange reaction of a dibromobiphenyl, such as 3,3'-dimethoxy-6,6'-dibromo-biphenyl, t-butyl-6,6'-dibromo-biphenyl, or 2,2'-dibromo-biphenyl with two equivalents of n-butyl lithium in ether at about 0° C. provided the corresponding dilithiated biphenyl which reacts with 0.5 equivalent of boron trifluoride etherate to yield the corresponding spiro borate, reference Formula I. The lithium ion may be replaced by various positive ions such as sodium, potassium, ammonium, tetraalkylammonium and the like by reacting the lithium salt with sodium methoxide, potassium chloride, ammonium chloride, tetraalkylammonium chloride and the like. Similarly, the borate salt of Schemes II or III can be prepared from 2,2'-dibromo-1,1'-binaphthyl or 1-(2'-bromophenyl)-2-bromonaphthyl, while the borate salt of Scheme III can be prepared from N-substituted 2,2'-dibromodiphenylamines; 2,2'-dibromophenyl ethers; and the like.

Specific examples of charge enhancing additive selected for the toner compositions of the present invention include the lithium, sodium potassium, cesium, ammonium and tetraalkylammonium salts of the following spiro borates: 5,5'-spirobi(5H-dibenzoborole), 2,2',8,8'-tetramethoxy-5,5'-spirobi(5H-dibenzoborole), 2,2',8,8'-tetraethoxy-5,5'-spirobi(5H-dibenzoborole), 3,3',7,7'-tetramethoxy-5,5'-spirobi(5H-dibenzoborole), 2,2',3,3',7,7',8,8'-octamethoxy-5,5'-spirobi(5H-dibenzoborole), 2,2',3,3',7,7',8,8'-octamethyl-5,5'-spirobi(5H-dibenzoborole), 2,2',8,8'-tetrafluoro-5,5'-spirobi(5H-dibenzoborole), 2,2',3,3',7,7',8,8'-octafluoro-5,5'-spirobi(5H-dibenzoborole), 2,2',8,8'-N,N,N',N'-octamethyltetraamino-5,5'-spirobi(5H-dibenzoborole), 3,3',7,7'-tetra-t-butyl-5,5'-spirobi(5H-dibenzoborole), 11,11'-siprobi[11H-benzo(c)dibenzoborole], and the like.

Illustrative examples of suitable toner resins selected for the toner and developer compositions of the present invention include polyamides, polyolefins, epoxies, polyurethanes, vinyl resins, including homopolymers or copolymers of two or more vinyl monomers; and polymeric esterification products of a dicarboxylic acid and a diol comprising a diphenol. Vinyl monomers include styrene, p-chlorostyrene, unsaturated mono-olefins such as ethylene, propylene, butylene, isobutylene and the like; saturated mono-olefins such as vinyl acetate, vinyl propionate, and vinyl butyrate; vinyl esters like esters of monocarboxylic acids including methyl acrylate, ethyl acrylate, n-butylacrylate, isobutyl acrylate, dodecyl acrylate, n-octyl acrylate, phenyl acrylate, methyl methacrylate, ethyl methacrylate, and butyl methacrylate; acrylonitrile, methacrylonitrile, acrylamide; styrene butadiene copolymers; and mixtures thereof.

As one preferred toner resin, there is the esterification products of a dicarboxylic acid and a diol comprising a diphenol. These resins are illustrated in U.S. Pat. No. 3,590,000, the disclosure of which is totally incorporated herein by reference. Other preferred toner resins include styrene/methacrylate copolymers, and styrene/butadiene copolymers; Pliolites; suspension polymerized styrene butadienes, reference U.S. Pat. No. 4,558,108, the disclosure of which is totally incorporated herein by reference; polyester resins obtained from the reaction of bisphenol A and propylene oxide; followed by the reaction of the resulting product with fumaric acid; and branched polyester resins resulting from the reaction of dimethylterephthalate, 1,3-butanediol, 1,2-propanediol, and pentaerythritol, styrene acrylates; and mixtures thereof. Also, waxes with a molecular weight of from about 1,000 to about 6,000 such as polyethylene, polypropylene, and paraffin waxes can be incorporated into the toner compositions as fuser roll release agents.

More specifically, there can be included in the toner compositions of the present invention low molecular weight waxes such as polypropylenes and polyethylenes commercially available from Allied Chemical and Petrolite Corporation; Epolene N-15, commercially available from Eastman Chemical Products, Inc.; Viscol 550-P, a low weight average molecular weight polypropylene available from Sanyo Kasei K.K.; and similar materials. The commercially available polyethylenes selected have a molecular weight of from about 1,000 to about 1,500, while the commercially available polypropylenes utilized for the toner compositions of the present invention are believed to have a molecular weight of from about 4,000 to about 5,000. Many of the polyethylene and polypropylene compositions useful in the present invention are illustrated in British Patent No. 1,442,835, the disclosure of which is totally incorporated herein by reference.

The low molecular weight wax materials are present in the toner composition of the present invention in various amounts, however, generally these waxes are present in the toner composition in an amount of from about 1 percent by weight to about 15 percent by weight, and preferably in an amount of from about 2 percent by weight to about 10 percent by weight.

The resin particles are present in a sufficient, but effective amount, for example from about 70 to about 90 weight percent, thus when 5 percent by weight of the charge enhancing additive is present, and 10 percent by weight of pigment or colorant, such as carbon black, is contained therein, about 85 percent by weight of resin is selected. Generally, from about 0.25 weight percent to about 10 weight percent, and preferably from about 1 weight percent to about 5 weight percent of the charge enhancing additive is selected for mixing with the toner particles; however, the charge enhancing additive of the present invention can be used in various other amounts providing the objectives of the present invention are accomplished. Also, the charge enhancing additive of the present invention may be coated on the pigment particles providing the objectives of the present invention can be achieved. When used as a coating, the charge enhancing additive of the present invention is present in an amount of from about 0.1 weight percent to about 5 weight percent, and preferably from about 0.3 weight percent to about 1 weight percent.

Numerous well known suitable pigments or dyes can be selected as the colorant for the toner particles including, for example, carbon black, nigrosine dye, aniline blue, magnetites, and mixtures thereof. The pigment, which is preferably carbon black, should be present in a sufficient amount to render the toner composition highly colored. Generally, the pigment particles are present in amounts of from about 3 percent by weight to about 20 percent by weight based on the total weight of the toner composition; however, lesser or greater amounts of pigment particles can be selected providing the objectives of the present invention are achieved.

When the pigment particles are comprised of magnetites, thereby enabling single component toners in some instances, which magnetites are a mixture of iron oxides ($FeO \cdot Fe_2O_3$) including those commercially available as Mapico Black, they are present in the toner composition in an amount of from about 10 percent by weight to about 70 percent by weight, and preferably in an amount of from about 10 percent by weight to about 50 percent by weight.

There can also be blended into the toner compositions of the present invention external additive particles including flow aid additives, which additives are usually present on the surface thereof. Examples of additives include colloidal silicas such as Aerosil, metal salts and metal salts of fatty acids inclusive of zinc stearate; aluminum oxides, cerium oxides and mixtures thereof, which additives are geneally present in an amount of from about 0.1 percent by weight to about 5 percent by weight, and preferably in an amount of from about 0.1 percent by weight to about 1 percent by weight. Several of the aforementioned additives are illustrated in U.S. Pat. Nos. 3,590,000 and 3,800,588, the disclosures of which are totally incorporated herein by reference.

With further respect to the present invention, the charge enhancing additives illustrated can be incorporated into the toner composition, preferably in an amount of 0.1 to about 10 weight percent, and more preferably from about 0.1 to 2 weight percent; or alternatively, colloidal silicas such as Aerosil are surface tesfted with the charge additives in an amount of from about 1 to about 30 weight percent and preferably 10 weight percent followed by the addition thereof to the toner in an amount of from 0.1 to 10 and preferably 0.1 to 1 weight percent.

Also encompassed within the scope of the present invention are colored toner and developer compositions comprised of toner resin particles, carrier particles, the charge enhancing additives illustrated herein, and as pigments or colorants red, green, blue, brown, magenta, cyan and/or yellow particles, as well as mixtures thereof. More specifically, with regard to the generation of color images utilizing a developer composition with the charge enhancing additives of the present invention, illustrative examples of magenta materials that may be selected as pigments include, for example, 2,9-dimethyl-substituted quinacridone and anthraquinone dye identified in the Color Index as Cl 60710, Cl Dispersed Red 15, diazo dye identified in the Color index as Cl 26050, Cl Solvent Red 19, and the like. Illustrative examples of cyan materials that may be used as pigments include colpper tetra-4(octadecyl sulfonamido) phthalocyanine, X-copper phthalocyanine pigment listed in the Color Index as Cl 74160, Cl Pigment Blue, and Anthrathrene Blue, identified in the Color Index as Cl 69810, Special Blue X-2137, and the like; while illustrative examples of yellow pigments that may be selected are diarylide yellow 3,3-dichlorobenzidene acetoacetanilides, a monoazo pigment identified in the Color Index as Cl 12700, Cl Solvent Yellow 16, a nitrophenyl amine sulfonamide identified in the Color Index as Foron Yellow SE/GLN, Cl Dispersed Yellow 33, 2,5-dimethoxy-4-sulfonanilide phenylazo-4'-chloro-2,5-dimethoxy aceto-acetanilide, and Permanent Yellow FGL. The aforementioned pigments are incorporated into the toner composition in various suitable effective amounts providing the objectives of the present invention are achieved. In one embodiment, these colored pigment particles are present in the toner composition in an amount of from about 2 percent by weight to about 15 percent by weight calculated on the weight of the toner resin particles.

For the formulation of developer compositions, there are mixed with the toner particles carrier components, particularly those that are capable of triboelectrically assuming an opposite polarity to that of the toner composition. Accordingly, the carrier particles of the present invention are selected to be of a positive polarity enabling the toner particles which are negatively charged to adhere to and surround the carrier particles. Illustrative examples of carrier particles include iron powder, steel, nickel, iron ferrites, silicon dioxide, and the like. Additionally, there can be selected as carrier particles nickel berry carriers as illustrated in U.S. Pat. No. 3,847,604, the disclosure of which is totally incorporated herein by reference. The selected carrier particles can be used with or without a coating, the coating generally containing terpolymers of styrene, methylmethacrylate, and a silane, such as triethoxy silane, reference U.S. Pat. Nos. 3,526,533 and 3,467,634, the disclosures of which are totally incorporated herein by reference; polymethyl methacrylates; other known coatings; and the like. The carrier particles may also include in the coating, which coating can be present in this embodiment in an amount of from about 0.1 to about 3 weight percent conductive substances, such as carbon black, in an amount of from about 5 to about 30 percent by weight. Polymer coatings not in close proximity in the triboelectric series ca also be selected, reference copending applications U.S. Ser. No. 136,791, and U.S. Ser. No. 136,792, the disclosures of which are totally incorporated herein by reference, including for example Kynar and polymethyl methacrylate. Coating weights can vary; generally, however, from about 0.1 to about 5, and preferably from about 1 to about 3 weight percent coating weight is selected.

Furthermore, the diameter of the carrier particles is generally from about 50 microns to about 1,000 microns thereby permitting them to possess sufficient density and inertia to avoid adherence to the electrostatic images during the development process. The carrier component can be mixed with the toner composition in various suitable combinations, however, best results are obtained when about 1 to 5 parts per toner to about 10 parts to about 200 parts by weight of carrier are selected.

The toner composition of the present invention can be prepared by a number of known methods including extrusion melt blending the toner resin particles, pigment particles of colorants, and the charge enhancing additive of the present invention; followed by mechanical attrition. Other methods include those well known in the art such as spray drying, melt dispersion, extrusion processing, dispersion polymerization, and suspension polymerization. Also, as indicated herein the toner composition without the charge enhancing additive can be prepared, followed by the addition of surface treated with charge additive, colloidal silicas.

The toner and developer compositions of the present invention may be selected for use in electrostatographic imaging apparatuses containing therein conventional photoreceptors providing that they are capable of being charged positively. This usually occurs with inorganic photoreceptors, illustrative examples of which include selenium, selenium alloys, such as selenium arsenic, selenium tellurium and the like; halogen doped selenium substances, and halogen doped selenium alloys. Also, the toner and developer compositions of the present invention can be used with layered photoreceptors that are capable of being charged negatively, such as those described in U.S. Pat. No. 4,265,990, the disclosure of which is totally incorporated herein by reference. For the latter members, normally the discharged areas are developed with the toner compositions of the present invention. Other similar photoreceptors can be selected providing the objectives of the present invention are achievable.

The toner compositions are usually jetted and classified subsequent to preparation to enable toner particles with a preferred average diameter of from about 5 to about 25 microns, and preferably from about 6 to about 15 microns. Also, the toner compositions of the present invention preferably triboelectric charge of from about 0.1 to about 3 femtocolumbs per micron as determined by the known charge spectograph. Admix time for the toners of the present invention is preferably from about less than 1 minute, and more specifically from about 15 to about 60 seconds as determined by the known charge spectograph.

The following examples are being supplied to further define various species of the present invention, it being noted that these examples are intended to illustrate and not limit the scope of the present invention. Parts and percentages are by weight unless otherwise indicated.

EXAMPLE I

There was prepared the charge additive lithium 2,2',8,8'-tetramethoxy-5,5'-spirobi(5H-dibenzoborole) in the following manner. Into an Erlenmyer flask was added acetic acid (50 milliliters), sodium acetate (8.0 grams) and 3,3'-dimethoxy-biphenyl (10 grams). The resulting mixture was then cooled with ice water. A solution of bromine (6 milliliters)/acetic acid (25 milliliters) was then added dropwise to the flask through an addition funnel. The resulting mixture was then stirred at room temperature for three hours and poured into an aqueous 0.1 percent $SnCl_2.2H_2O$ solution (500 milliliters). Subsequently, the resulting mixture was stirred for one hour and substantially all of the water was removed by decantation. To the resulting wet solid slurry was added 5 percent $Na_2CO_3$ (200 milliliters). The mixture was then stirred for 30 minutes and then filtered by suction to provide the crude product (16 grams) which was then recrystallized from ethanol to provide the dibrominated product 2,2'-dibromo-5,5'-dimethoxybiphenyl (13 grams) as white crystals. A portion of the product obtained (3.7 grams) was added into a 100 milliliter addition storage funnel containing a magnetic stirring bar. The funnel was capped with a rubber septum and then placed onto one of the side necks of a 100 milliliter three-necked flask (14/20 joint) equipped with a condenser, a rubber septum and a magnetic stirrer. The aforementioned system was repeatedly (three times) evacuated and then purged with dried nitrogen. Ether (25 milliliters) was syringed into the aforementioned obtained dibromo compound to form a solution. To this was dropwise added n-butyl lithium (9 milliliters, 2.5M in hexane) via a gas tight syringe. The resulting mixture was stirred for four hours at room temperature and then added gradually to an ethereal solution of boron trifluoride etherate (0.64 milliliter in 10 milliliters of ether). The resulting mixture was heated to reflux for 10 hours and then filtered. The solid resulting was added to water (15 milliliters) and then filtered to remove the insoluble material. The filtrate was allowed to dry in air and the resulting solid (1.8 grams) was recrystallized from methanol to provide the above charge enhancing additive compound lithium 2,2',8,8'-tetramethoxy-5,5'-spirobi(5H-dibenzoborole) (1.4 grams, 58 percent based on the dibromo compound) as pale yellow crystals (mp >260° C., dec. (decomposition)).

EXAMPLE II

Preparation of lithium 5,5'-spirobi(5H-dibenzoborole). Into a 250 milliliter three-necked flask equipped with an addition funnel, a condenser and a magnetic stirrer was added triphenyl-phosphine (29.5 grams) and acetonitrile (60 milliliters). The mixture was cooled with ice water before the dropwise addition of bromine (17.5 grams) via the funnel. The resulting mixture was stirred at room temperature for 30 minutes. A solution of o,o'-biphenol (9.3 grams in 30 milliliters acetonitrile) was then added to the flask. The resulting mixture was heated to reflux for three hours. Thereafter, the resulting solution was transferred into a 250 milliliter one-necked round bottom flask, and the solvent was removed by distillation under the pressure of a water aspirator. The mixture was headed to 250° C. for 30 minutes and then at 300° C. for one hour. The residue was distilled under vacuo (0.2 millimeter Hg/120° C., bath temperature 180° to 200° C.) through a short path distillation head to provide a colorless oil (7.5 grams) which solidified quickly afterwards. The product resulting was recrystallized from ethanol to provide o,o'-dibromobiphenyl (5.5 grams) as white needles. A portion of this (3.1 grams) was selected to prepare the above charge additive compound by repeating the procedure as described in Example I. The crude product (1.3 grams) was recrystallized from $CHCl_3$/methanol to yield a white powder (0.8 gram, 45 percent; mp >270° C., dec.) of lithium 5,5'-spirobi(5H-dibenzoborole).

EXAMPLE III

A slurry of 5 grams of the colloidal silica Aerosil R972, available from Degussa Inc., in 250 milliliters of acetone was mixed thoroughly within an explosion-proof Waring blender. Subsequently, the above prepared charge additive compounds of Examples I or II, 0.5 gram, 10 weight percent, and 150 milliliters of acetone were added to the slurry and mixed for about 10 minutes in the blender. The mixture resulting was then transferred to a round bottom flask and evaporated to dryness by heating to 40° C. on a rotoevaporator. The resulting residual solid was then dried in a vacuum oven for 10 hours, and thereafter placed in a blender equipped with a four blade agitator and fluffed to a powdery consistency of surface treated Aerosil with the charge additive of Examples I or II.

EXAMPLE IV

A magenta developer was prepared as follows. A toner composition was prepared by melt blending in an extruder at about 100° C. 90 parts by weight of a styrene butadiene resin (89/11), and 10 parts by weight of a mixture of 5 parts of Hostaperm Pink, available from American Hoechst, and 5 parts by weight of a styrene n-butylmethacrylate resin (58/42). The formed toner was micronized, followed by classification yielding toner particles with a volume average diameter of 9 microns. To the resulting toner particles was added to the treated colloidal silica charge additive of Example III with the charge additive of Example I in an amount of 0.5 weight percent.

Subsequently, carrier particles were prepared by the solution coating of a Hoeganoes Anchor steel core with a particle diameter of from 75 to 150 microns with 1 part by weight of a coating comprising 20 parts by weight of carbon black Vulcan 72 R, available from Cabot Corporation, homogeneously dispersed in 80 parts by weight of polymethacrylate, which coating was solution coated from a toluene solvent. A magenta developer was then prepared by blending 97.5 parts by weight of the prepared coated carrier particles with 2.5 parts by weight of the above prepared toner in a lab blender for 10 minutes resulting in a developer with the characteristics as recited in Table I that follows.

EXAMPLE V

A cyan developer was prepared as follows. A toner composition was prepared by melt blending in an extruder at about 100° C. 45 parts by weight of a styrene butadiene resin (89/11), 45 parts by weight of a styrene n-butylmethacrylate resin (58/42) and 7.5 parts by weight of Sudan Blue OS available from BASF. The formed toner was micronized, followed by classification yielding toner particles with a volume average diameter of 9 microns. To the resulting toner particles was added the surface treated colloidal silica charge additive (Example I) of Example III in an amount of 0.5 weight percent.

Subsequently, carrier particles were prepared by the solution coating of a Hoeganoes Anchor steel core with a particle diameter of from 75 to 150 microns with 1 part by weight of a coating comprising 20 parts by weight of carbon black Vulcan 72 R, available from Cabot Corporation, homogeneously dispersed in 80 parts by weight of polymethacrylate, which coating was solution coated from a toluene solvent. A cyan developer was then prepared by blending 97.5 parts by weight of the coated carrier particles with 2.5 parts by weight of the above prepared toner in a lab blender for 10 minutes resulting in a developer with the characteristics as recited in Table I that follows.

EXAMPLE VI

A black nonmagnetic developer was prepared as follows. A toner composition was prepared by melt blending in an extruder at about 100° C. 94 parts by weight of styrene butadiene resin (89/11), and 6.0 parts by weight of Regal 330 ® carbon black available from Cabot Corporation. The formed toner was micronized, followed by classification yielding toner particles with a volume average diameter of 9 microns. To the resulting toner particles was added the treated colloidal silica charge additive of Example IV in an amount of 0.5 weight percent.

Subsequently, carrier particles were prepared by the solution coating of a Hoeganoes Anchor steel core with a particle diameter of from 75 to 150 microns with 1 part by weight of a coating comprising 20 parts by weight of carbon black Vulcan 72 R, available from Cabot Corporation, homogeneously dispersed in 80 parts by weight of polymethylacrylate, which coating was solution coated from a toluene solvent. A black developer was then prepared by blending 97.5 parts by weight of the coated carrier particles with 2.5 parts by weight of the above prepared toner in a lab blender for 10 minutes resulting in a developer with the characteristics as recited in Table I that follows.

EXAMPLE VII

A black magnetic developer was prepared as follows. A toner composition was prepared by melt blending in an extruder at about 100° C. 79 parts by weight of a styrene butadiene resin (89/11), 5.0 parts by weight of Regal 330 ® carbon black available from Cabot Corporation, and 16 weight percent of the magnetite Mapico Black. The formed toner was micronized, followed by classification yielding toner particles with a volume average diameter of 9 microns. To the resulting toner particles was added the colloidal silica charge additive of Example IV in an amount of 0.5 weight percent.

Subsequently, carrier paticles were prepared by the solution coating of a Hoeganoes Anchor steel core with a particle diameter of from 75 to 150 microns with 1 part by weight of a coating comprising 20 parts by weight of carbon black Vulcan 72 R, available from Cabot Corporation, homogeneously dispersed in 80 parts by weight of polymethylacrylate, which coating was solution coated from a toluene solvent. A magnetic black developer was then prepared by blending 97.5 parts by weight of the coated carrier particles with 2.5 parts by weight of the above prepared toner in a lab blender for 10 minutes resulting in a developer with the characteristics as recited in Table I that follows.

Thereafter, the aforementioned magenta developer compositions were incorporated into the Xerox Corporation 4050 TM xerographic imaging apparatus with a layered photoresponsive member comprised of an aluminum supporting substrate, a photogenerating layer of trigonal selenium, and a charge transport layer comprised of 55 percent by weight of molecules of N,N'-diphenyl-N,N'-bis(3-methylphenyl)-1,1-biphenyl-4,4'-diamine dispersed in 45 percent by weight of a polycarbonate resin commercially available as Makrolon, reference U.S. Pat. No. 4,265,990, the disclosure of which has been totally incorporated herein by reference, which imaging member was negatively charged; and contained latent images thereon (development accomplished by discharge area development) and there resulted 300 magenta images of excellent resolution and with no background deposits.

TABLE I

| DEVELOPER ADMIX | CHARGING RESULTS | | |
|---|---|---|---|
| | SURFACE ADDITIVE | Q/D FC/MICRON | ADMIX MINUTES |
| Magenta(control)* | 0.50% Aerosil | 1.17 | 2.0 |
| Magenta(control) | 0.25% Aerosil | −0.77 | >5.0 |
| Magenta** | 0.50% | −0.57 | 1.0 |
| Magenta** | 0.25% | −0.77 | 2.0 |
| Magenta** | 0.50% | −0.59 | 1.0 |
| Cyan(control) | 0.50% Aerosil | −1.25 | 5.0 |
| Cyan(control) | 0.25% Aerosil | −1.05 | >5.0 |
| Cyan** | 0.50% | −0.39 | 0.5 |
| Cyan** | 0.25% | −0.65 | 1.0 |
| Cyan** | 0.5% | −0.77 | 1.0 |
| Black(control) | 0.50% Aerosil | −1.30 | 5.0 |
| Magnetic(control) | 0.25% Aerosil | −1.10 | >5.0 |
| Black** | 0.50% | −0.50 | 0.5 |
| Magnetic** | 0.25% | −0.81 | 2.0 |
| Black** | 0.50% | −0.78 | 1.0 |
| Magnetic** | 0.25% | −0.85 | 2.0 |
| Black Magnetic (control) | 0.50% Aerosil | −0.88 | >5.0 |
| Black Magnetic** | 0.50% | −0.62 | 0.5 |
| Black Magnetic** | 0.50% | −0.60 | 1.0 |

*Control - the developer of the Example with no negative charge control additive.
**For these developers of the present invention, the additive of Example III with the charge additive of Example I was selected at the amounts indicated.

Other modifications of the present invention will occur to those skilled in the art based upon a reading of the disclosure of the present application and these modifications are intended to be included within the scope of the present invention.

What is claimed is:

1. A negatively charged toner composition comprised of resin particles, pigment particles, and as a charge enhancing additive the salts of 5,5'-spirobi(5H-dibenzoborole) of the following Formulas I, II, III, IV, or V:

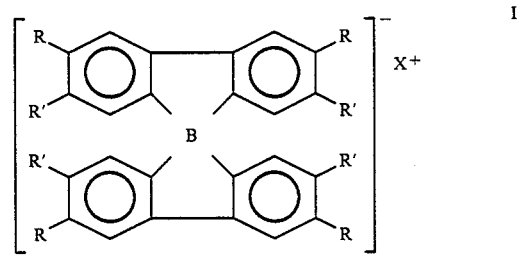

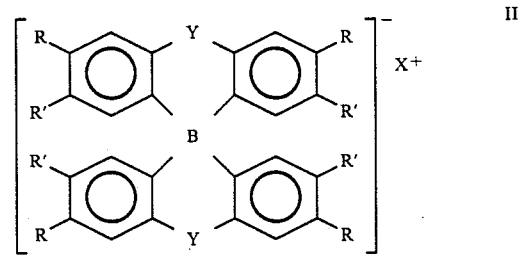

-continued

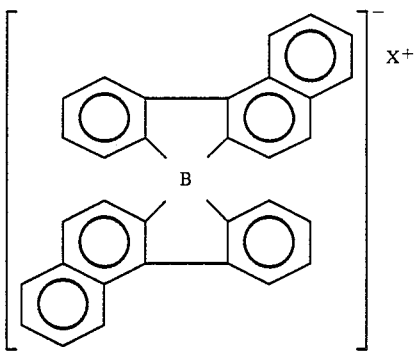

III

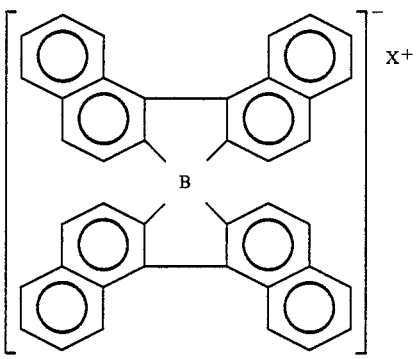

IV

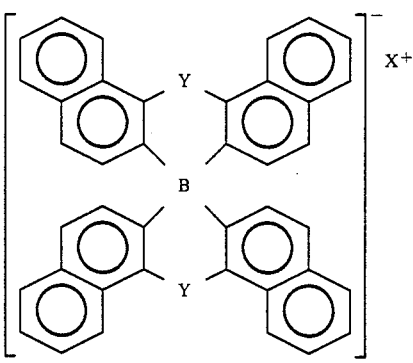

V wherein R, and R' are independently selected from the group consisting of hydrogen, an aliphatic group, and halide; Y is alkylene or hetroatoms; and X is a cation.

2. A toner in accordance with claim 1 wherein the aliphatic group is alkyl, alkoxy, substituted alkyl, or substituted alkoxy.

3. A toner composition in accordance with claim 1 wherein R and R' are independently selected from the group consisting of hydrogen, methyl, ethyl and $CH_3(CH_2)_n$, wherein n is a number of 2 to about 20.

4. A toner composition in accordance with claim 1 wherein X is an alkali metal, ammonium, or $NR_4$ wherein R is alkyl.

5. A toner composition in accordance with claim 4 wherein the alkali metal is selected from the group consisting of lithium, sodium, potassium, magnesium, calcium, and barium.

6. A toner composition in accordance with claim 1 wherein the charge enhancing additives are the salts of 5,5'-spirobi(5H-dibenzoborole), 2,2',8,8'-tetramethoxy-5,5'-spirobi(5H-dibenzoborole), 3,3',7,7'-tetra-t-butyl-5,5'-spirobi(5H-dibenzoborole), 2,2',8,8'-tetrafluoro-5,5'-spirobi(5H-dibenzoborole), or 2,2',3,3',7,7',8,8'-octamethoxy-5,5'-spirobi(5H-dibenzoborole).

7. A toner composition in accordance with claim 1 wherein a colloidal silica is treated with the charge enhancing additive.

8. A toner composition in accordance with claim 1 wherein the charge enhancing additive is present in an amount of from about 1 to about 10 percent by weight.

9. A toner composition in accordance with claim 1 wherein the resin particles are comprised of styrene polymers, polyesters, or mixtures thereof.

10. A toner composition in accordance with claim 1 containing a wax component with a weight average molecular weight of from about 1,000 to about 6,000.

11. A toner composition in accordance with claim 10 wherein the waxy component is selected from the group consisting of polyethylene and polypropylene.

12. A toner composition in accordance with claim 1 containing as external additives metal salts of a fatty acid, colloidal silicas, or mixtures thereof.

13. A toner composition in accordance with claim 1 wherein the pigment particles are carbon black, magnetites, or mixtures thereof; cyan, magenta, yellow, red, blue, green, brown, and mixtures thereof.

14. A developer composition comprised of the toner composition of claim 1 and carrier particles.

15. A developer composition in accordance with claim 14 wherein the carrier particles are comprised of ferrites, or an iron powder.

16. A developer composition in accordance with claim 14 wherein the carrier particles are comprised of a core with a polymer coating thereover.

17. A developer composition in accordance with claim 16 wherein the coating is comprised of a methyl terpolymer, or a polymethyl methacrylate, or a mixture of polymers not in close proximity in the triboelectric series.

18. A method of imaging which comprises formulating an electrostatic latent image on a photoreceptor, affecting development thereof with the toner composition of claim 1, and thereafter transferring the developed image to a suitable substrate.

19. A method of imaging in accordance with claim 18 wherein the transferred image is permanently fixed to the substrate.

20. A method of imaging which comprises formulating an electrostatic latent image on a positively or negatively charged photoreceptor, affecting development thereof with the toner composition of claim 1, and thereafter transferring the developed image to a suitable substrate.

21. A method of imaging in accordance with claim 20 wherein the transferred image is permanently fixed to the substrate.

22. A toner in accordance with claim 1 wherein the halide is fluoride, chloride, bromide, or iodide.

23. A toner in accordance with claim 1 wherein alkylene is methylene.

24. A toner in accordance with claim 1 wherein the hetroatoms are oxygen, sulfur, nitrogen, or alkylated nitrogen.

25. A single component negatively charged toner composition comprised of resin particles, magnetite components, and as a charge enhancing additive the salts of 5,5'-spirobi(5H-dibenzoborole) anions of the following Formulas I, II, III, IV, or V:

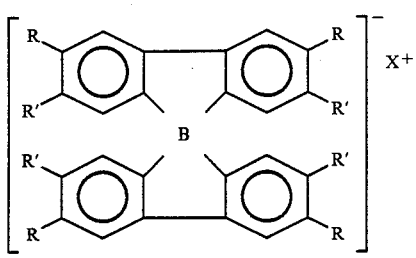
I
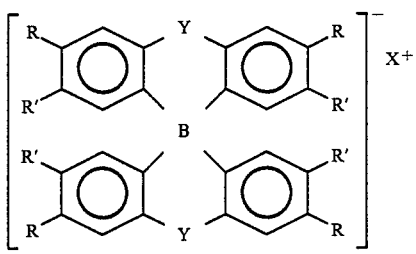
II
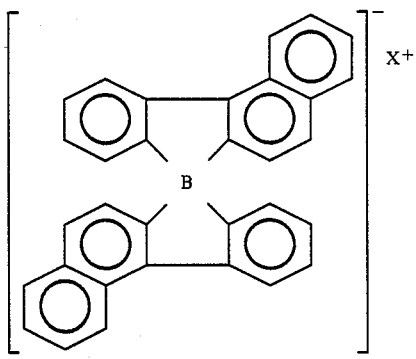
III
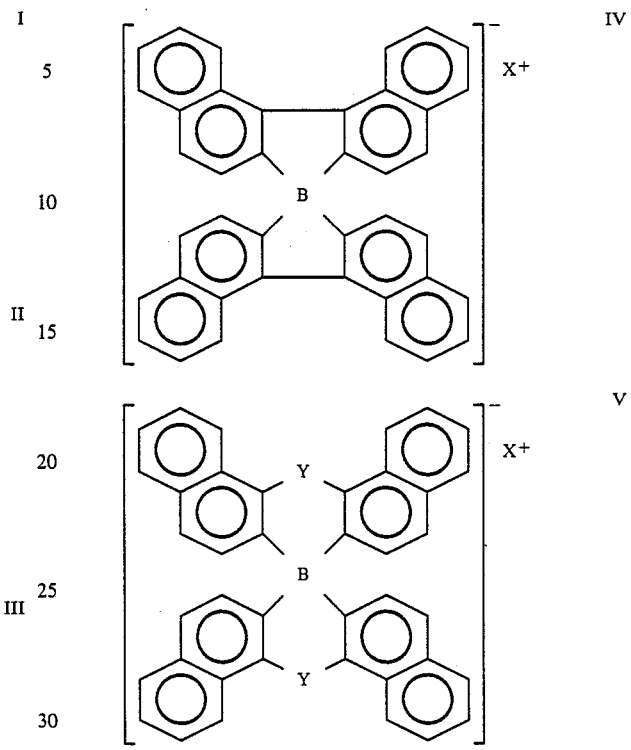
wherein R and R' are independently selected from the group consisting of hydrogen, an aliphatic group, and halide; Y is alkylene or hetroatoms; and X is a cation.
26. A toner in accordance with claim 1 wherein the charge enhancing additive is present on the surface subsequent to sorption on colloidal silica particles.
* * * * *